United States Patent [19]

Meyer et al.

[11] 4,455,426
[45] Jun. 19, 1984

[54] TETRAHYDROPYRIMIDINE-ISOCYANATE ADDITION PRODUCTS

[75] Inventors: Rolf-Volker Meyer; Hans J. Kreuder, both of Krefeld; Eckhard de Cleur, Duisburg, all of Fed. Rep. of Germany

[73] Assignee: Bayer Aktiengesellschaft, Leverkusen, Fed. Rep. of Germany

[21] Appl. No.: 428,852

[22] Filed: Sep. 30, 1982

Related U.S. Application Data

[62] Division of Ser. No. 317,299, Nov. 2, 1981, Pat. No. 4,424,353.

[30] Foreign Application Priority Data

Nov. 6, 1980 [DE] Fed. Rep. of Germany ....... 3041834

[51] Int. Cl.³ .................. C07D 239/06; C07D 239/70; C08G 59/18
[52] U.S. Cl. ..................................... 544/253; 544/335
[58] Field of Search ................ 544/335, 253, 243, 242

[56] References Cited

U.S. PATENT DOCUMENTS

| | | | |
|---|---|---|---|
| 4,024,259 | 5/1977 | Bauer et al. | 424/251 |
| 4,147,737 | 4/1979 | Sein et al. | 428/418 X |
| 4,258,186 | 3/1981 | Schott et al. | 544/253 |
| 4,404,302 | 9/1983 | Gupta et al. | 544/335 |
| 4,404,379 | 9/1983 | Hajek et al. | 544/335 |

FOREIGN PATENT DOCUMENTS

| | | |
|---|---|---|
| 2163962 | 6/1972 | Fed. Rep. of Germany . |
| 2722514 | 11/1978 | Fed. Rep. of Germany . |
| 2731335 | 1/1979 | Fed. Rep. of Germany . |
| 2751805 | 5/1979 | Fed. Rep. of Germany . |
| 1585455 | 3/1981 | United Kingdom . |

OTHER PUBLICATIONS

Corfield, et al., Chemical Abstracts, vol. 64, 12563d, (1966).
Wendelin, et al., Chemical Abstracts, vol. 92, 22455d, (1980).

*Primary Examiner*—Donald G. Daus
*Assistant Examiner*—Diana G. Rivers
*Attorney, Agent, or Firm*—Connolly and Hutz

[57] ABSTRACT

New amidine/isocyanate adducts are particularly useful as catalysts for hardening epoxy resins, in particular pulverulent coating compositions based on epoxy resins. New bicyclic amidines are excellent starting materials for manufacturing these amidine/isocyanate adducts.

2 Claims, No Drawings

TETRAHYDROPYRIMIDINE-ISOCYANATE ADDITION PRODUCTS

This application is a division of application Ser. No. 317,299 filed Nov. 2, 1981, now U.S. Pat. No. 4,424,353.

This invention relates to new bicyclic amidines and new amidine/isocyanate adducts and to processes for the preparation thereof and to the use thereof as catalysts for hardening epoxide resins, i.e. thermosetting compounds based on polyepoxides and optionally polymers containing carboxylic groups. The properties of the amidine/isocyanate adducts according to the present invention are particularly useful when these substances are used as hardeners for powder lacquer binders.

Pulverulent coatings which may be applied to a substrate by whirl sintering, flame spraying or the electrostatic powder spray process are known. They should be capable of being converted into cross-linked coatings by a stoving treatment carried out at moderately high temperatures for as short a time as possible. It should be borne in mind that, while there is a demand for ever shorter stoving times at lower temperatures, which means higher reactivity, no reaction should take place between the resin and hardener when the mixture of binder, pigments, fillers and optionally other auxiliary agents is extruded at temperatures of from 80° to 160° C., preferably from 90° to 120° C.

Although it is possible to equip the resin component with such a large number of carboxyl groups that complete reaction is achieved under stoving conditions of from 150° to 160° C./30 minutes, the high acid number causes an unwanted preliminary reaction to take place even during the extrusion process and this reaction may only be kept within tolerable limits by vigorous cooling of the extrudate. The storage stability is also impaired since an unwanted reaction takes place even at room temperature and adversely affects the levelling of the powder lacquer and/or the mechanical properties of the stoved lacquer coat.

A powder lacquer binder consisting of a carboxyl group-containing polyester and triglycidyl isocyanurate has been disclosed in German Offenlegungsschrift No. 2,163,962 (see Claim 4). Binders of this type are said to produce weather-resistant (chalking-resistant) lacquer coats. The stoving conditions of such systems are normally 200° C./10 minutes or 160° C./30 minutes for layer thicknesses of from 40 to 120 μm. There has therefore been a demand for powder lacquers which may be hardened under more favourable conditions without any loss in levelling properties or storage stability.

It has now surprisingly been found that catalysts based on certain isocyanate-masked amidines are capable of withstanding unharmed the extrusion of the starting components to powder lacquers ready for use and do not become active until the final heat hardening process.

Guanidines are to be regarded as a sub-class of amidines for the purposes of the present invention and will therefore also be referred to as "amidines".

The present invention relates to bicyclic amidines corresponding to the following general formula:

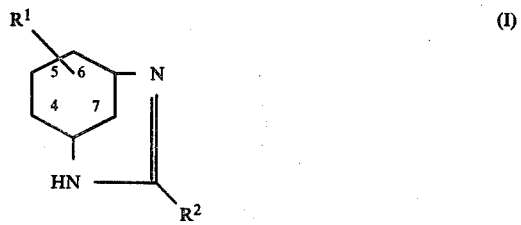

wherein

R¹ represents a hydrogen atom or an alkyl group having from 1 to 4 carbon atoms, preferably a hydrogen atom or a methyl group; and R² represents a hydrogen atom, an alkyl group having from 1 to 18 carbon atoms, a cycloalkyl group having from 5 to 14 carbon atoms, an aralkyl group having from 7 to 16 carbon atoms or an aryl group having from 6 to 20 carbon atoms.

The following compounds are preferred amidines (I):

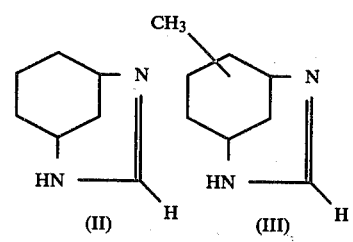

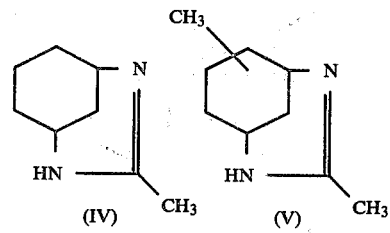

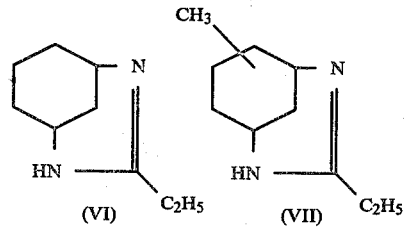

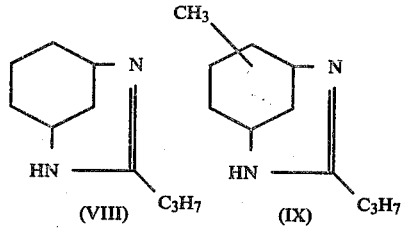

-continued

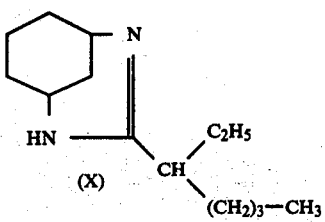
(X)

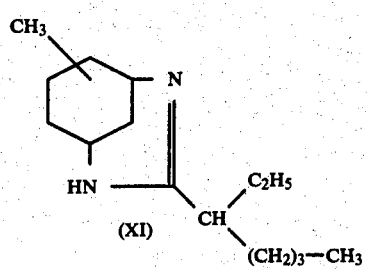
(XI)

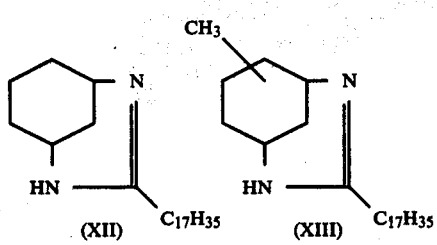
(XII)   (XIII)

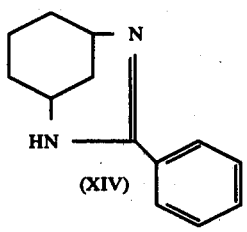
(XIV)

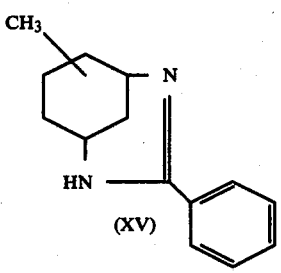
(XV)

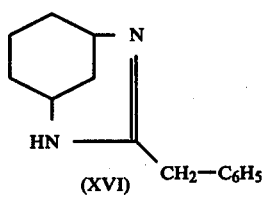
(XVI)

-continued

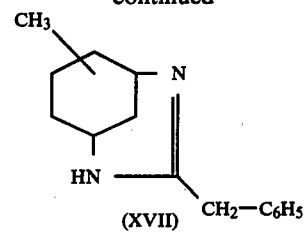
(XVII)

The above formulae indicated by odd Roman numerals are abbreviated forms of representing the four different isomers in which the methyl group is in the 4-, 5-, 6- and 7-position, respectively. 4- and 7-methyl derivatives are preferred.

The amidines (I) may be prepared by known methods, preferably by reaction of cycloaliphatic diamines (XVIII) with monocarboxylic acids (XIX) which are preferably saturated or with the reactive derivatives thereof (XIX):

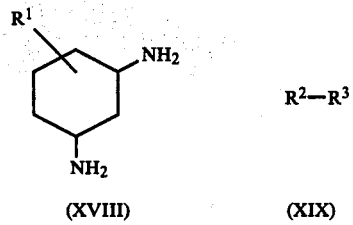

(XVIII)    (XIX)

wherein
$R^1$ and $R^2$ are as defined above;
$R^3$ represents COCl, CN, or $CO_2R^4$; and
$R^4$ represents a hydrogen atom, $C_1$–$C_6$ alkyl, phenyl or benzyl.

Apart from 1,3-diaminocyclohexane itself, preferred compounds (XVIII) include in particular the methyl-1,3-diaminocyclohexanes formed by hydrogenation of tolylene diamines which are obtainable on a large technical scale. The 2,4- and 2,6-diaminoisomers and mixtures thereof are equally suitable.

Preferred carboxylic acids (XIX) include formic acid, acetic acid, propionic acid, butyric acid, 2-ethyl hexanoic acid, stearic acid, benzoic acid and phenyl acetic acid.

The present invention also relates to a process for the preparation of amidines (I) from the compounds (XVIII) and (XIX), characterised in that compounds (XVIII) and (XIX) are reacted in proportions corresponding to from 2.5 mol, preferably from 1 to 1.5 mol, of diamine (XVIII) per mol of carboxylic acid (derivative) group of compound (XIX) at from 150° to 280° C., preferably from 200° to 250° C., for from 2 to 10 hours.

The excess of diamine (XVIII) has been found to be advantageous since it is less favourable to the formation of the corresponding diamide. It is advisable to use a catalyst in some cases.

Although bicyclic amidines (I) are known from German Offenlegungsschrift No. 2,722,514 (formula Ic on page 8), the formula in question covers 5-membered rings, as well as 6- and 7-membered rings, and since these compounds known from the literature are accelerators for the preparation of polyureas, the literature gives no indication that the amidines (I) according to the present invention may be used in an isocyanate-masked form as catalysts for the hardening of epoxide resins.

Amidines of the imidazole-type and the use thereof for bonding thermosetting one-component epoxide systems have been disclosed in German Offenlegungsschrift No. 2,731,335, but these imidazolines are in most cases insufficiently reactive for hardening powder lacquers based on epoxide resins.

Amidines of the tetrahydropyrimidine-type and the use thereof for blocking polyisocyanates have been described in German Offenlegungsschrift No. 2,751,805. The blocked polyisocyanates are said to be suitable as catalysts for the anionic polymerisation of ε-caprolactam and the preparation of wire lacquers. Amidines (I) according to the present invention are neither described nor in any way suggested in German Offenlegungsschrift No. 2,751,805.

The present invention also relates to addition products obtainable from polyisocyanates, preferably from polyisocyanates having from 4 to 25, in particular from 4 to 16, carbon atoms and from 2 to 4, preferably 2, isocyanate groups, and amidines (I).

Preferred polyisocyanates for the reaction with amidines (I) to form isocyanate addition products include aliphatic, cycloaliphatic, araliphatic, i.e. aryl-substituted aliphatic, and/or aromatic diisocyanates, such as those described in "Methoden der organischen Chemie" (Houben-Weyl), Vol. 14/2, 4th Edition; Georg Thieme-Verlag, Stuttgart 1963, pages 61–70, and by W. Siefken, Liebigs Ann. Chem. 562, 75–136, e.g. the following: 1,2-ethylene diisocyanate, 1,4-tetramethylene diisocyanate, 1,6-hexamethylene diisocyanate, 2,2,4- and 2,4,4-trimethyl-1,6-hexamethylene diisocyanate, 1,12-dodecane diisocyanate,107,ω-diisocyanatodipropyl ether, cyclobutane-1,3-diisocyanate, cyclohexane-1,3- and 1,4-diisocyanate, 2,2- and 2,6-diisocyanato-1-methyl cyclohexane, 3-isocyanatomethyl-3,5,5-trimethyl cyclohexyl isocyanate ("isophorone diisocyanate"), 2,5- and 3,5-bis-(isocyanatomethyl)-1,4-methano-decahydronaphthalene, 1,5-, 2,5- 1,6- and 2,6-bis-(isocyanato-methyl)-4,7-methano-hexahydroindane, 1,5-, 2,5-, 1,6- and 2,6-bis-(isocyanato)-4,7-methano-hexahydroindane, dicyclohexyl-2,4'- and 4,4'-diisocyanate, 2,4- and 2,6-hexahydrotolylenediisocyanate, perhydro-2,4'- and 4,4'-diphenylmethanediisocyanate, ω,ω'-diisocyanato-1,4-diethylbenzene, 1,3- and 1,4- phenylene diisocyanate, 4,4'-diisocyanatodiphenyl, 4,4'-diisocyanato-3,3'-dichlorodiphenyl, 4,4'-diisocyanato-3,3'-dimethoxydiphenyl, 4,4'-diisocyanato-3,3'-dimethyl-diphenyl, 4,4'-diisocyanato-3,3'-diphenyldiphenyl, 2,4'- and 4,4'-diisocyanato-diphenylmethane, naphthylene-1,5-diisocyanate, mixtures of tolylene diisocyanates, 2,4- and 2,6-tolylene diisocyanate, N,N'-(4,4'-dimethyl-3,3'-diisocyanatodiphenyl)-uretdione and m-xylylenediisocyanate, but also triisocyanates, such as 2,4,4'-triisocyanatodiphenyl ether, 4,4'-4"-triisocyanatotriphenyl methane and tris-(4-isocyanatophenyl)-thiophosphate, and mixtures of these isomers may also be used.

As a general rule, it is particularly preferred to use commercially readily available aliphatic, cycloaliphatic or aromatic diisocyanates, in particular hexamethylene diisocyanate, 3-isocyanatomethyl-3,5,5-trimethyl-cyclohexylisocyanate and 2,4- and 2,6-tolylene diisocyanate and isomeric mixtures thereof.

Other preferred polyisocyanates for the preparation of the amidine/polyisocyanate addition products are the prepolymers obtainable from the above-mentioned polyisocyanates and polyhydric alcohols having from 2 to 12 carbon atoms and from 2 to 6 OH groups. Other preferred polyisocyanates are formed by auto-addition of some of the above-mentioned polyisocyanates. They may contain biuret, uretdione, uretone imine, isocyanurate, urea and/or allophanate groups in addition to the free isocyanate groups.

The present invention further relates to a process for the preparation of the above-mentioned addition products, characterised in that the amidines (I) and polyisocyanates are reacted at from 50° to 150° C., preferably from 80° to 120° C., in proportions providing from 0.8 to 3, preferably from 0.95 to 1.5, isocyanate groups per NH group of the amidines (I).

It goes without saying that whichever of the components is more easily dosed at the reaction temperature employed should be added to the heated reactant in the reaction vessel. Liquid polyisocyanates are therefore preferably added to the liquid amidine (I).

The reaction may be carried out with or without inert solvents. Preferred solvents include ketones, such as acetone, methyl ethyl ketone, methyl isobutyl ketone, cyclopentanone and cyclohexanone; aromatic solvents, such as benzene, toluene, xylenes, chlorobenzene and nitrobenzene; cyclic ethers, such as tetrahydrofuran and dioxane; esters, such as methyl acetate and n-butyl acetate; aliphatic chloro-hydrocarbons, such as chloroform and carbon tetrachloride; and aprotic solvents, such as dimethyl formamide, dimethyl acetamide and dimethyl sulphoxide.

After termination of the reaction, the solvent may be removed and the resulting amidine/polyisocyanate addition products according to the present invention are discharged and converted into a form suitable for further use.

The amidine/polyisocyanate adducts according to the present invention generally have a particular molecular weight resulting from the nature and quantity of the starting components. If a polyisocyanate mixture containing molecules having differing molecular weights is used, the addition products obtained have a particular molecular weight distribution. They have in most cases an average molecular weight $\overline{M}_n$ of from 200 to 3000, preferably from 300 to 1000, (determined by vapour pressure osmometry in acetone) and melt in the region of from 30° to 220° C., preferably from 80° to 160° C. (DIN 53 180).

The present invention also relates to addition products obtainable from monoisocyanates having from 2 to 20 carbon atoms and amidines which contain at least once the structure:

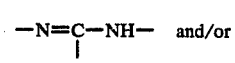 and/or 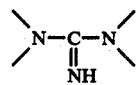

(XX)    (XXI)

Preferred monoisocyanates include alkyl, cycloalkyl, aralkyl and aryl isocyanate having from 2 to 20 carbon atoms, e.g. the following:
methyl isocyanate,
ethyl isocyanate,
propyl isocyanate,
butyl isocyanate,
2-ethyl-hexyl isocyanate,
6-chlorohexyl isocyanate, stearyl isocyanate,
phenyl isocyanate, and
benzyl isocyanate.

The less volatile isocyanates having at least 6 carbon atoms are preferably used, in particular 6-chlorohexyl isocyanate and stearyl isocyanate.

Among the above-mentioned amidines (XX) and (XXI), amidines (I) are particularly preferred. Other preferred amidines (XX) and (XXI) are the imidazolines corresponding to the following general formula:

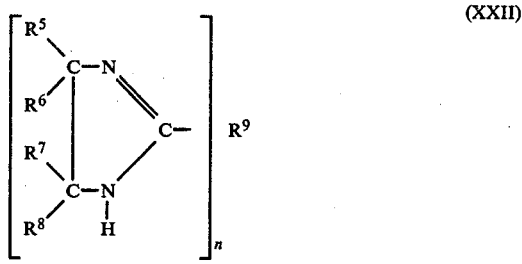

(XXII)

wherein $R^5$, $R^6$, $R^7$ and $R^8$ independently represent a hydrogen atom, an alkyl group having from 1 to 6 carbon atoms, a cycloalkyl group having from 5 to 10 carbon atoms, an aralkyl group having from 7 to 12 carbon atoms, an aryl group having from 6 to 15 carbon atoms or a heterocyclic group having from 5 to 10 carbon atoms and 1 or 2 oxygen and/or nitrogen and/or sulphur atoms; and $R^9$ represents an alkyl or alkylene group having from 1 to 6 carbon atoms, an aryl or arylene group having from 6 to 15 carbon atoms, each of which may be substituted by alkyl, cycloalkyl, aralkyl, aryl or heterocyclic groups (as defined for $R^5$, $R^6$, $R^7$ and $R^8$);

n represents 1 or 2; and $R^9$ may also represent a hydrogen atom when n represents 1.

The following are examples of preferred imidazolines (XXII): 2-phenyl-imidazoline, 2-phenyl-4-methyl-imidazoline, 2-(m-tolyl)-4-methyl-imidazoline, 2-(m-pyridyl)-imidazoline, 1,4-tetramethylene-bis-(4-methyl-imidazoline-2), 2-methyl-imidazoline, 2,4-dimethyl-imidazoline, 2-ethyl-imidazoline, 2-ethyl-4-methyl-imidazoline, 2-benzyl-imidazoline, 2-(o-tolyl)-imidazoline, 2-(p-tolyl)-imidazoline, tetramethylene-bis-imidazoline, 1,1,3-trimethyl-1,4-tetramethylene-bis-imidazoline, 1,1,3-trimethyl-1,4-tetramethylene-bis-4-methyl-imidazoline, 1,3,3-trimethyl-1,4-tetramethylene-bis-4-methyl-imidazoline, 1,2-phenylene-bis-imidazoline, 1,3-phenylene-bis-4-methyl-imidazoline. Mixtures of the imidazoline derivatives may also be used. 2-phenyl-imidazoline and 2-methyl-imidazoline are particularly preferred.

Preferred amidines (XX) and (XXI) also include tetrahydropyrimidines corresponding to the following general formula:

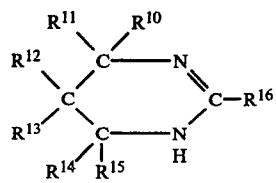

(XXIII)

wherein $R^{10}$ to $R^{16}$ independently represent a hydrogen atom, an alkyl group having from 1 to 6 carbon atoms, a cycloalkyl group having from 5 to 10 carbon atoms, an aralkyl group having from 7 to 12 carbon atoms or an aryl group having from 6 to 15 carbon atoms, and two geminal or vicinal substituents, together with the carbon atom to which they are attached, may also complete a cycloaliphatic ring having 5 or 6 carbon atoms.

The following are examples of preferred tetrahydropyrimidines (XXIII): 2-methyl-tetrahydropyrimidine, 2,4-, 2,5- and 2,6-dimethyl-tetrahydropyrimidine, 2-ethyl-tetrahydropyrimidine, 2-ethyl-4-methyl-tetrahydropyrimidine, 2-benzyl-tetrahydropyrimidine, 2-phenyl-tetrahydropyrimidine, 2-phenyl-4-methyl, -5-methyl- and -6-methyl-tetrahydropyrimidine, 2,4-diaza-3-phenyl-7,9,9- and 7,7,9-trimethyl-bicyclo-(4,3,0)-nonene-2, and 2,4-diaza-3-methyl-7,9,9- and 7,7,9-trimethyl-bicyclo(4,3,0)-nonene-2 and mixtures thereof.

Preferred amidines (XX) and (XXI) also include compounds corresponding to the following general formula:

(XXIV)

wherein $R^{17}$, $R^{18}$ and $R^{19}$ have the same definition as $R^5$ to $R^8$, but $R^{17}$ and $R^{18}$ are not members of a common ring.

The following are examples of preferred amidines (XXIV): formamidine, acetamidine, caproylamidine, benzamidine, benzyliminocaprolactam, n-butyl and t-butyliminocaprolactam, N-ethyl-N'-benzyl-benzamidine, N-t-butyl-N'-benzyl-acetamidine and N-n-butylamino-N'-benzyl acetamidine.

The preferred amidines (XX) and (XXI) also include guanidines corresponding to the following general formula:

(XXV)

$R^{20}$, $R^{21}$, $R^{22}$ and $R^{23}$ independently represent a hydrogen atom, a $C_1$-$C_{12}$ alkyl group, a $C_5$-$C_{12}$ cycloalkyl group, a $C_7$-$C_{12}$ aralkyl group, a $C_6$-$C_{12}$ aryl group or a $C_1$-$C_{12}$ acyl group, preferably a $C_1$-$C_4$ alkyl group or phenyl group.

The following are examples of preferred guanidines (XXV):
N-methyl-guanidine,
N-ethyl-guanidine,
N-butyl-guanidine, N-methyl-N'-ethyl-guanidine,
N,N'-dimethyl-guanidine,
N,N'-diethyl-guanidine,
N-methyl-N'-isopropyl-guanidine,
N,N'-dibutyl-guanidine,
N,N,N'-trimethyl-guanidine,
N,N,N',N'-tetramethyl-guanidine,
N,N,N',N'-tetraethyl-guanidine,
N-phenyl-guanidine,
N,N'diphenyl-guanidine,
N,N'-ditolyl-guanidine,
N-formyl-guanidine and
N-butyryl-guanidine.

The present invention also relates to a process for the preparation of the above-mentioned amidine/monoisocyanate addition products, characterised in that the amidines (XX) or (XXI) and the mono-isocyanates having from 2 to 20 carbon atoms are reacted at from 50° to 130° C., preferably from 80° to 110° C., in proportions providing from 0.8 to 1.1, preferably ca. 1, isocyanate group per NH group of the amidines (XX) or (XXI).

As regards the use of a solvent, the same rules apply as for the amidine/polyisocyanate addition products.

The present invention further relates to the use of the amidine/polyisocyanate and amidine/monoisocyanate addition products according to the present invention as catalysts for hardening thermosetting epoxide resins, in particular for hardening pulverulent coating compounds based on polyepoxides and optionally polymers containing carboxyl groups.

The catalysts according to the present invention are generally used in quantities of from 0.1 to 5%, by weight, preferably from 1 to 2%, by weight, based on the sum of epoxide resin and any acid polymer present (exception see page 26). Addition of the catalyst is preferably carried out at the stage of preparation of the finished powder lacquer system by extrusion.

The polyepoxides which may be used are solid, in most cases resinous substances which melt in the range of from 30° to 140° C., preferably from 40° to 80° C., (determined by the method of differential thermoanalysis), and contain, on average, more than one 1,2-epoxy group per molecule.

The polyepoxide compounds may be based on polyhydric phenols, such as pyrocatechol, resorcinol, hydroquinone, 4,4'-dihydroxy-diphenyl methane, 4,4'-dihydroxy-3,3'-dimethyl-diphenyl methane, 4,4'-dihydroxy-diphenyldimethyl methane (bisphenol A), 4,4'-dihydroxy-diphenylmethyl methane, 4,4'-dihydroxy-diphenyl-cyclohexane, 4,4'-dihydroxy-3,3'-dimethyl-diphenyl propane, 4,4'-dihydroxydiphenyl, 4,4'-dihydroxy-diphenyl sulphone, tris-(4-hydroxy-phenyl)-methane, chlorination and bromination products of the above-mentioned diphenols, in particular of bisphenol A; novolaks (i.e. reaction products of monohydric or polyhydric phenols with aldehydes, in particular formaldehyde, in the presence of acid catalysts), diphenols obtained by esterification of 2 mols of the sodium salt of an aromatic hydroxy-carboxylic acid with 1 mol of a dihalo alkane or dihalo dialkyl ether (see British Pat. No. 1,017,613), and polyphenols obtained by the condensation of phenols with long-chain halogenated paraffins containing at least two halogen atoms (see British Pat. No. 1,024,288).

It is preferred to use commercially available solid epoxide resins of the type of diglycidyl ethers of bisphenol A (i.e. reaction products of bisphenol A and epichlorohydrin) having an epoxide equivalent of from 400 to 2500.

Compounds, such as (poly)glycidyl esters corresponding to the following general formula:

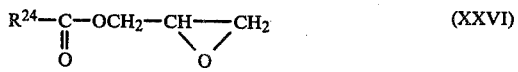

wherein $R^{24}$ represents a straight- or branched-chain saturated or unsaturated hydrocarbon group having from 4 to 20 carbon atoms or a substituted or unsubstituted phenyl group, may also be used.

Compounds which may be used according to the present invention also include triglycidyl isocyanurate and/or its oligomers and triglycidyl urazole and its oligomers, and mixtures thereof.

The polymers containing carboxyl groups may be polyester polycarboxylic acids prepared from polyols and polycarboxylic acids or derivatives thereof.

The polymers containing carboxyl groups should have a melting and softening range (determined by differential thermoanalysis) of from 20° to 150° C., preferably from 50° to 100° C., and an acid number of from 10 to 150, preferably from 20 to 120, in particular from 30 to 50. The OH numbers should preferably be below 20, in particular below 10.

The esterification reaction to synthesise the polyester carboxylic acids may be carried out by known methods of esterification of the corresponding polycarboxylic acids and polyols, in particular of dicarboxylic acids and dihydric alcohols, or by ester formation from suitable derivatives of these alcohols and carboxylic acids, such as the anhydrides, acid chlorides or hydroxy carboxylic acids.

Particularly preferred polyester polycarboxylic acids, i.e. those which are at least trifunctional, are obtained by the incorporation of polycarboxylic acids or anhydrides thereof which are at least trifunctional, such as benzene-1,3,5-tricarboxylic acid or trimellitic acid anhydride.

Branched-chain polyester polycarboxylic acids may also be used. These may be obtained by the incorporation of preferably aliphatic polyols containing at least three hydroxyl groups, such as trimethylol propane or glycerol.

Suitable polycarboxylic acids for the preparation of the polyester polycarboxylic acids to be used according to the present invention include in particular those corresponding to the following general formula:

wherein A represents a bond or an x-valent, substituted or unsubstituted aliphatic group preferably having from 1 to 20 carbon atoms, a cycloaliphatic group preferably having from 5 to 16 carbon atoms, an aliphatic-aromatic group preferably having from 7 to 20 carbon atoms, an aromatic group preferably having from 6 to 15 carbon atoms or an aromatic or cycloalphatic group having from 2 to 12 carbon atoms and containing hetero-atoms, such as N, O or S in the ring; and x represents an integer of from 2 to 4, preferably 2 or 3.

The following are preferred examples of such polycarboxylic acids: oxalic acid, malonic acid, succinic acid, glutaric acid, adipic acid, trimethyladipic acid, azelaic acid, sebacic acid, decane dicarboxylic acid, dodecane dicarboxylic acid, fumaric acid, maleic acid, hexahydroterephthalic acid, phthalic acid, isophthalic acid, terephthalic acid, benzene-1,3,5-tricarboxylic acid, benzene-1,2,4-tricarboxylic acid, benzene-1,2,3-tricarboxylic acid, naphthalene-1,5-dicarboxylic acid, benzophenone-4,4'-dicarboxylic acid, diphenyl-sulphone-4,4'-dicarboxylic acid, butane-tetracarboxylic acid, tricarballylic acid, ethylene tetracarboxylic acid, pyromellitic acid, benzene-1,2,3,4-tetracarboxylic acid, benzene-1,2,3,5-tetracarboxylic acid and the acids corresponding to the following general formulae:

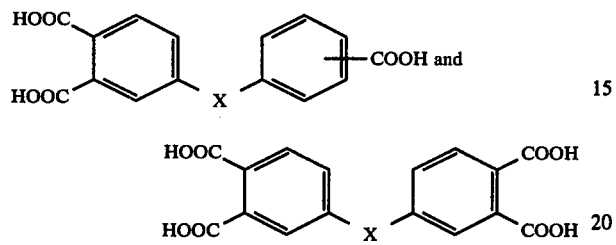

wherein X represents

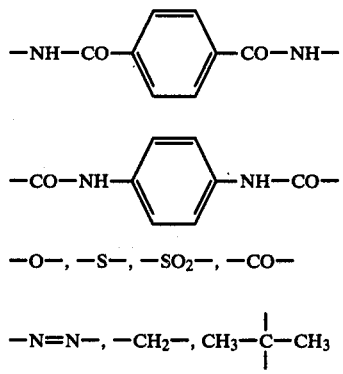

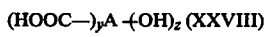

The hydroxycarboxylic acids are preferably those corresponding to the following general formula:

(HOOC—)$_y$A—(OH)$_z$ (XXVIII)

wherein A is as defined above; and y and z may represent, independently of each other, an integer of from 1 to 3, preferably 1 or 2.

Preferred examples are: glycollic acid, lactic acid, mandelic acid, malic acid, citric acid, tartaric acid, 2-, 3- and 4-hydroxybenzoic acid and hydroxybenzene-dicarboxylic acids.

The polyols required for the preparation of the polyester polycarboxylic acids include in particular those corresponding to the following general formula:

B(—OH)$_a$      XXIX wherein B represents an a-valent aliphatic group having from 2 to 20 carbon atoms, a cycloaliphatic group having from 5 to 16 carbon atoms, an araliphatic group having from 7 to 20 carbon atoms, an aromatic group, having from 6 to 15 carbon atoms or a heterocyclic group having from 2 to 12 carbon atoms containing N, O or S; and a represents an integer of from 2 to 6, preferably 2 or 3.

The following are preferred examples of such polyols: ethylene glycol, 1,2- and 1,3-propane diol, 1,2, 1,3-, 1,4- and 2,3-butane diol, 1,5-pentane diol, 2,2-dimethyl-1,3-propane diol, 1,6- and 2,5-hexane diol, 1,12-dodecane diol, 1,12-octanedecane diol, 2,2,4- and 2,4,4-trimethyl-1,6-hexane diol, trimethylol propane, trimethylol ethane, glycerol, 1,2,6-hexane triol, pentaerythritol, mannitol, 1,4-bis-hydroxymethylcyclohexane, cyclohexane-1,4-diol, 2,2-bis-(4-hydroxycyclohexyl)-propane, bis(4-hydroxyphenyl)-methane, bis-(4-hydroxyphenyl)-sulphone, 1,4-bis-hydroxymethylbenzene, 1,4-dihydroxy benzene, 2,2-bis-(4-hydroxyphenyl)-propane, 1,3-bis-hydroxyalkyl hydantoin, tris-hydroxyalkyl-isocyanurate and tris-hydroxyalkyltriazolidine-3,5-dione.

Further examples of polyols suitable for the preparation of the polyester polycarboxylic acids include the hydroxyalkyl ethers corresponding to the following general formula:

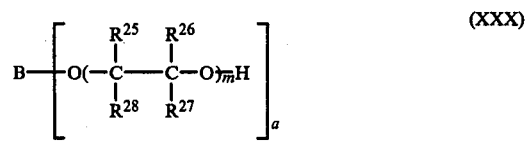

(XXX)

obtained by the addition of substituted or unsubstituted alkylene oxides, such as ethylene oxide, propylene oxide, butylene oxide or styrene oxide, to the above-mentioned polyols.

In the above general formula, B and a are as defined above; m represents an integer of from 1 to 7; and $R^{25}$, $R^{26}$, $R^{27}$ and $R^{28}$ independently represent a hydrogen atom, a $C_1$-$C_{10}$ aliphatic group optionally substituted with halogen, a $C_4$-$C_8$ cycloaliphatic group, a $C_7$-$C_{17}$ araliphatic group or a $C_6$-$C_{16}$ aromatic group optionally substituted with halogen and/or alkyl and/or alkoxy. $R^{25}$, $R^{26}$, $R^{27}$ and $R^{28}$ preferably represent hydrogen, an alkyl group having from 1 to 4 carbon atoms, preferably methyl or ethyl, or a $C_6$-$C_{12}$ aryl group optionally substituted with one or more halogen atoms (in particular chlorine and/or bromine) and/or $C_1$-$C_4$ alkyl groups and/or $C_1$-$C_4$ alkoxy groups, but in particular they represent phenyl.

The following are preferred examples of such polyols: diethylene glycol, triethylene glycol, dipropylene glycol, tripropylene glycol, dibutylene glycol, 1,4-bis/2-hydroxy-ethoxy/-cyclohexane, 1,4-bis/2-hydroxy-ethoxymethane/-cyclohexane, 1,4-bis/2-hydroxy-ethoxy/-benzene, 4,4'-bis/2-hydroxyethoxy/-diphenylmethane, -diphenylpropane-2, diphenyl ether, -diphenyl sulphone, -diphenyl ketone and -diphenyl cyclohexane.

The carboxylic acids or carboxylic acid derivatives and polyols used may, of course, also be polymeric. Thus, for example, bis-benzene-dicarboxylic acid esters corresponding to the following general formula:

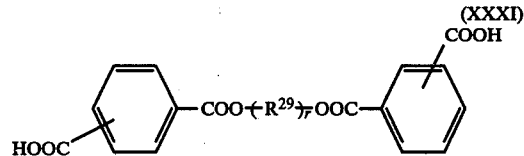

(XXXI)

and bis-alkane-dicarboxylic acid esters corresponding to the following general formula:

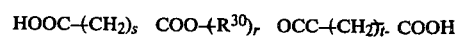

may be used.

In the above general formulae, $R^{29}$ and $R^{30}$ independently represent an at least divalent aromatic group having from 6 to 15 carbon atoms, an araliphatic group having from 7 to 20 carbon atoms, a saturated or unsaturated aliphatic group having from 2 to 20 carbon atoms, or a cycloaliphatic group having from 5 to 15 carbon atoms, which may be condensed with aromatic ($C_6$–$C_{12}$), cycloaliphatic ($C_4$–$C_{12}$) or heterocyclic ($C_2$–$C_{12}$) ring systems and connected through ether, keto, ester or sulpho bridges and may be substituted by halogen or by nitro or alkoxy groups having from 1 to 20 carbon atoms; r represents an integer of from 1 to 20; and s and t, which may be the same or different, represent zero or an integer of from 1 to 20.

The following are preferred examples of $(R^{29})_r$ and $(R^{30})_r$:

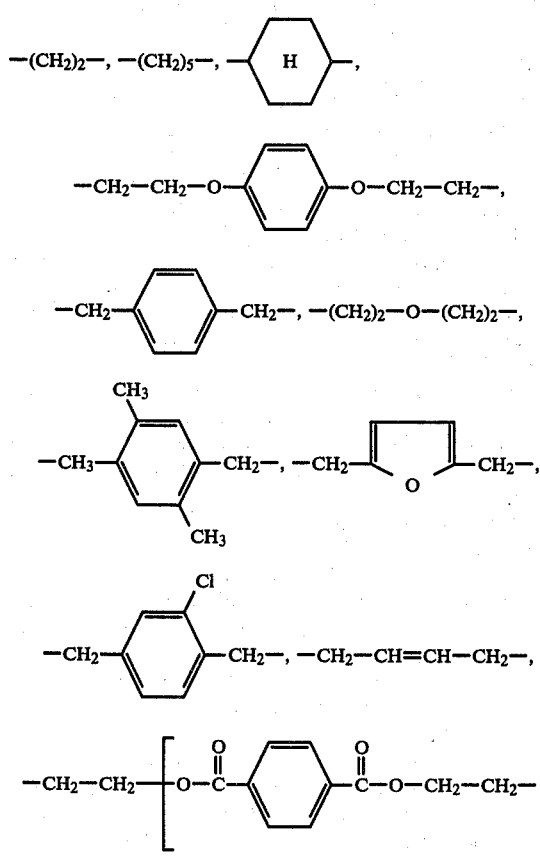

$u = 1$–$7$.

These polyester polycarboxylic acids may be prepared by known methods, generally by melting the polycarboxylic acids and polyols together and removing the water, liberated, possibly by application of a vacuum or by purging with nitrogen. The progress of the reaction may be followed by titration of the excess carboxyl groups so that the end of the reaction may easily be determined.

Hydroxyl polyesters prepared by known methods from polycarboxylic acids, anhydrides, acid chlorides and/or alkyl esters and polyols may, of course, also be reacted with polycarboxylic acids and anhydrides to produce the polyester polycarboxylic acids. Such polyesters, containing hydroxyl groups, may of course, also be reacted with low molecular weight acid polyesters, i.e. polyesters containing carboxyl groups, to produce the polyester polycarboxylic acids.

Where branched-chain polyester polycarboxylic acids are required, these may be prepared by condensing all the components by solvent-free condensation in the presence of an at least trifunctional alcohol or an at least trifunctional polycarboxylic acid by the methods described above to produce a branched-chain polyester.

Alternatively, the at least trifunctional polyol may be reacted with the dicarboxylic acids or derivatives thereof to form a short-chain polyester containing carboxyl groups or derivatives thereof, which polyester is then condensed with further diols and dicarboxylic acids to form the polyester polycarboxylic acids.

An at least trifunctional polycarboxylic acid may, of course, also react with diols to form a branched, short-chain polyester containing hydroxyl groups, which may then be further reacted with diols and dicarboxylic acids to produce the polyester polycarboxylic acids used according to the present invention.

Branched chain polyester polycarboxylic acids may, of course, also be obtained by reacting polycarboxylic acids which are at least partially trifunctional with the above-described polyesters containing hydroxyl groups.

Another group of polymers containing carboxyl groups are the carboxyl group-containing copolymers consisting of copolymerised units of from 2 to 25 parts, by weight, of at least one copolymerisable $\alpha,\beta$-ethylenically unsaturated carboxylic acid having from 3 to 5 carbon atoms and from 75 to 98 parts, by weight, of at least one further copolymerisable monomer. The $\alpha,\beta$-ethylenically unsaturated carboxylic acids may be mono- or dicarboxylic acids, or semi-esters of dicarboxylic acids having from 1 to 12 carbon atoms in the alcohol component.

The following are preferred copolymerisable monomers:

(I) Maleic acid diesters and esters of acrylic or methacrylic acid with $C_1$–$C_{12}$ aliphatic, $C_5$ or $C_6$ cycloaliphatic or $C_7$ or $C_8$ araliphatic monohydric alcohols; for example, methyl acrylate, ethyl acrylate, n-propyl acrylate, isopropyl acrylate, n-butyl acrylate, t-butyl acrylate, 2-methylhexyl acrylate, 2-ethylhexyl acrylate, dodecyl acrylate, and the corresponding methacrylic acid esters and maleic acid diesters; cyclopentyl acrylate, cyclohexyl acrylate or the corresponding methacrylic acid esters and maleic acid diesters; benzyl acrylate, $\beta$-phenyl ethyl acrylate and corresponding methacrylic acid esters and maleic acid diesters;

(II) Aromatic vinyl and vinylidene compounds, for example, styrene, $\alpha$-methyl styrene, $\alpha$-methyl-p-isopropyl styrene, $\alpha$-methyl-m-isopropyl styrene, o, an p-chlorostyrene, o- and p-bromostyrene, methyl styrenes substituted in the nucleus, p-t-butyl styrene and mixtures thereof;

(III) Vinyl ester of organic monocarboxylic acids in which the acid component has from 2 to 4 carbon atoms, such as vinyl acetate and vinyl propionate;

(IV) Mono-olefinically unsaturated halogenated hydrocarbons, such as vinyl chloride or vinylidene chloride, preferably vinyl chloride;

(V) Acrylonitrile, methacrylonitrile, acrylamide and methacrylamide;

(VI) Vinyl alkyl ethers having from 1 to 4 carbon atoms in the alkyl group, such as vinyl methyl ether, vinyl ethyl ether, vinyl propyl ether and vinyl butyl ether.

Preferred copolymers containing carboxyl groups consist of polymerised units of:
(a) from 0 to 60%, by weight, of styrene, α-methyl styrene, o- or p-chlorostyrene, o or p-bromostyrene, p-t-butyl styrene or mixtures thereof, preferably styrene;
(b) from 0 to 98%, by weight, of acrylic acid esters having $C_1$-$C_8$ aliphatic alcohol groups or methacrylic acid esters having $C_1$-$C_8$ aliphatic alcohol groups, or mixtures thereof; and
(c) from 2 to 25%, by weight, of acrylic acid, methacylic acid, itaconic, maleic and fumaric acid semiesters having from 1 to 8 carbon atoms in the alcohol component, or mixtures thereof, preferably acrylic acid and/or methacrylic acid;
the sum of the percentage contents of (a) to (c) being 100. Instead of (c), the copolymer may contain from 2 to 25% by weight, of at least one olefinically unsaturated copolymerisable monomer containing hydroxyl groups, such as hydroxyalkyl esters of acrylic, methacrylic, maleic, fumaric or itaconic acid having from 2 to 4 carbon atoms in the alcohol group.

When monomers containing hydroxyl groups are used, the copolymers obtained contain hydroxyl groups and may be converted into copolymers containing carboxyl groups by a reaction with carboxylic acid anhydrides, such as succinic acid anhydride.

The term "copolymers" is used here to denote not only copolymers having a statistical distribution of the polymerised monomers or block copolymers, but also graft copolymers in which monomers are grafted on a previously formed homo- or co-polymer. Statistical copolymers are preferred.

The carboxyl group-containing copolymers used according to the present invention are prepared by known methods, such as solvent-free, solution, dispersion or bead polymerisation, preferably by solution polymerisation or solvent-free polymerisation. Such methods have been described, for example in "Methoden der Organischen Chemie", (Houben-Weyl), 4th Edition, Volume 14/1, pages 24 to 556, Georg Thieme Verlag, Stuttgart, 1961, and in German Offenlegunsschrift Nos. 2,600,318 and 1,965,740.

The quantities of the individual components of the powder lacquer binder may be widely varied.

When the epoxide resins used are exclusively (i.e. in the absence of carboxyl polyesters) of the type of diglycidyl ethers of bisphenol A having a melting point of from 50° to 120° C. and an epoxide equivalent of from 400 to 2000, the conventional catalysts, such as dicyandiamide, benzimidazole or guanidine, may advantageously be replaced by the amidine/isocyanate addition products according to the present invention, using proportions, by weight, of resin to catalyst of from 99:1 to 85:15, preferably from 97:3 to 88:12.

When however mixtures of epoxide resins of the type of diglycidyl esters of bisphenol A and carboxyl polyesters are used, the proportions in the mixture depend on the acid number of the carboxyl polyester. Thus, for example, if the acid number is from 30 to 40, the proportion, by weight, of epoxide resin/carboxyl polyester is usually from 60:40 to 80:20, preferably 70:30. If the carboxyl polyester has a higher acid number, e.g. from 40 to 110, the conventional proportion, by weight, of epoxide resin to carboxyl polyester used in practice is from 40:60 to 60:40, preferably ca. 50:50.

When using carboxyl polyesters which are hardened by the admixture of triglycidyl isocyanurate (TGIC) and/or triglycidyl urazole (TGUZ) and/or glycidyl esters, the resin/hardener ratio also depends on the acid number of the carboxyl polyester. Thus, the proportion by weight, of carboxyl polyesters having an acid number from 30 to 40 to hardeners, such as TGIC and/or TGUZ and/or glydicyl esters, is from 90:10 to 95:5. Carboxyl polyesters having higher acid numbers, such as from 40 to 100, generally require the addition of a higher proportion of hardener so that the proportion, by weight, of carboxyl polyesters to hardeners, such as TGIC and/or TGUZ and/or glycidyl esters is from 88:12 to 92:8.

Other possible components of powder lacquers, such as pigments, dyes, fillers, levelling agents, agents to render the lacquers thixotropic, dearating agents, UV stabilisers, oxidation inhibitors and quenchers (radical acceptors, such as N-alkyl-substituted piperidines), matting agents and substances which improve the surface smoothness, may be varied within a wide range.

Preparation of powder lacquers is usually carried out as follows: The chosen binders are first mixed with the amidine/isocyanate addition compounds according to the present invention and optionally other additives and then homogenised solvent-free. This may be carried out in suitable apparatus, such as heated kneaders, but is preferably carried out by extrusion at a temperature which causes a maximum shearing force to act on the mixture. The upper limit of temperature should not exceed 140° C.

When the extruded mass has been cooled to room temperature and suitably size reduced, it is ground down to a powder lacquer, the aim being to reduce it to particles having an average size of from 40 to 70 $\mu$m, preferably ca. 50 $\mu$m, depending on the purpose for which the powder is to be used. Any coarse particles measuring more than 100 $\mu$m are removed by screening.

Application of the powder lacquers prepared as described above to suitable substrates may be carried out by known methods, such as electrostatic powder spraying, whirl sintering, electrostatic whirl sintering, flame spraying or by the application of an aqueous suspension using conventional or electrical methods.

After application of the powder lacquer by one of the methods mentioned above, the coated workpieces are heated to temperatures of 140° C. or above to harden the lacquer, the heating time depending to a large extent on the thermal capacity of the coated workpiece or its temperature before coating.

The advantage obtainable according to the present invention resides in a considerable reduction in the so-called "stoving time" and/or lowering of the stoving temperature.

When the isocyanate-masked amidines according to the present invention are used as hardener compounds for powder lacquers based on epoxide resins of the type of diglycidyl ethers of bisphenol A, additional advantages include the excellent compatibility of the resin component with the amidine/isocyanate adducts according to the present invention, which in this case act as hardeners, with the result that a high degree of gloss is achieved. In addition, the preparation of the powder lacquer is facilitated due to the absence of unwanted preliminary reaction between resin and hardener during the extrusion process since splitting of the amidine/isocyanate adducts generally does not occur at the given residence time of the mixture in the extruder and at the extrusion temperature required.

A further advantage compared with the use of known hardeners, such as dicyandiamide, amines or guanidines, is to be seen in the fact that significantly better levelling may be achieved according to the present invention. The same advantages of using the amidine/isocyanate adducts described are also obtained analogously when the powder lacquer binder used is not an epoxide resin of the type of diglycidyl ether of bisphenol A, but a mixture thereof with a suitable carboxyl polyester or if for the purpose of obtaining weather-resistant coatings a conventional carboxyl polyester is used as binder containing, as hardener component, TGIC and/or TGUZ and/or suitable glycidyl esters. The amidine/isocyanate adducts described in both cases act as latent catalysts. In the latter case there is also the problem of reducing the energy requirement for stoving by lowering the stoving temperature and/or reducing the stoving time. The problem could hitherto only be solved by adding catalysts which had a deleterious effect on the levelling of the coatings and/or reduced the stability of the coating compound in storage.

The parts indicated in the following Examples are parts by weight.

EXAMPLES

I. Preparation of the amidine corresponding to Formula (A) (A:)

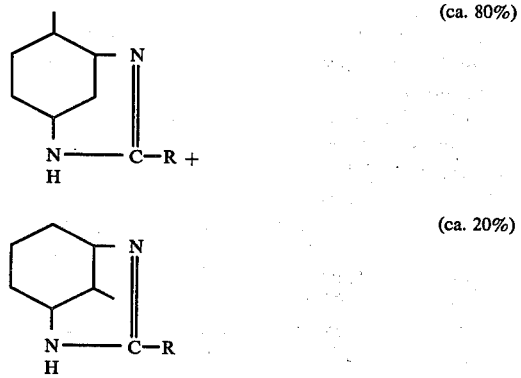

EXAMPLE 1

Preparation of the amidine corresponding to Formula (A) wherein R represents phenyl 768 g (6 mol) of 2,4-diamino(methyl-cyclohexane)(-mixture) of isomers), hereinafter referred to as "PH-tolamine", and 200 ml of water are introduced with stirring and under nitrogen as protective gas into a 4-liter three-necked flask equipped with stirrer, thermometer and Claisen bridge with a 1 l receiver flask. 732 g (6 mol) of benzoic acid are added portion-wise in the course of 30 minutes. The temperature rises to 80° C. The reaction mixture is then rapidly heated to 250° C. and water and excess PH-tolamine distil off. The reaction is terminated after 4 hours at 250° C. The distillate contains 250 g of PH-tolamine and water. The reaction product left behind is distilled at ca. 0.3 mbar (up to 240° C.). 733 g of crude product solidifying to yellowish crystals and 346 g of residue are obtained. Distillation of the crude product yields the following fractions:

First fraction b.p.$_{0.3\ mbar}$ 80°–160° C.=35 g (ca. 90% PH-tolamine).

Main fraction b.p.$_{0.3\ mbar}$ 160°–195° C.=671 g amidine, white crystals m.p. 50°–60° C., residue 27 g.

EXAMPLE 2

Preparation of the amidine corresponding to Formula (A) wherein R represents H 736 g (16 mol) of formic acid are added portion-wise over a period of 2 hours to 2048 g (16 mol) of PH-tolamine and 400 ml of water analogously to Example 1. The temperature rises to 90° C. The reaction mixture is then rapidly heated to 250° C., and water and excess PH-tolamine distil off. The reaction is completed after 4 hours' stirring at 250° C. The distillate contains 806 g of PH-tolamine and water. The reaction product remaining behind is distilled at ca. 0.3 mbar (up to 200° C.). 806 g of crude product (yellow oil, b.p.$_{0.3\ mbar}$ 102°–170° C.) are obtained. The residue weighs 480 g. Distillation of the crude product yields the following fractions:

First fraction b.p.$_{0.3\ mbar}$ 35°–107° C.=139 g (90% PH-tolamine)

Main fraction b.p.$_{0.3\ mbar}$ 107°–130° C.=595 g

Yellowish oil which gradually solidifies to a resin having a softening point of from 45°–55° C. Residue 62 g.

EXAMPLE 3

Preparation of the adduct of stearyl isocyanate and the amidine from Example 1

59 g (0.2 mol) of stearyl isocyanate are added portion-wise over a period of 20 minutes to 49 g (0.2 mol based on the equivalent weight) of the amidine of Example 1 with stirring under nitrogen as protective gas at from 100° to 120° C. in a 250 ml three-neck flask equipped with stirrer, thermometer, reflux condenser and dropping funnel. An almost colourless resin having a softening point of ca. 35° C. is obtained.

EXAMPLE 4

Preparation of the adduct of stearyl isocyanate and the amidine from Example 2

73.7 g (0.25 mol) of stearyl isocyanate are added portion-wise in the course of 20 minutes to 34.5 g (0.25 mol) of the amidine from Example 2 at from 100° to 120° C. in a manner analogous to Example 3. A brownish resin is obtained, which is ground to an almost colourless powder having a softening point of ca. 35° C.

EXAMPLE 5

Preparation of the adduct of tetramethyl guanidine and 6-chlorohexyl isocyanate 80.5 g (0.5 mol) of 6-chlorohexyl isocyanate are added portion-wise over a period of 20 minutes to 57.0 g (0.5 mol) of tetramethyl guanidine with stirring under nitrogen as protective gas at from 105° to 110° C. in a 250 ml three-necked flask equipped with stirrer, thermometer, reflux condenser and dropping funnel. The slightly exothermic reaction is completed after a further 30 minutes' stirring at 110° C. A slightly yellowish resin having a softening point ca. of 35° C. is obtained. The isocyanate content is 0.5%, by weight.

EXAMPLE 6

Preparation of the adduct of hexamethylene diisocyanate and the amidine from Example 1

42 g (0.25 mol) of hexamethylene diisocyanate are added portion-wise over a period of 30 minutes to 122.5 g (0.5 mol) of the amidine from Example 1 at from 120° to 150° C. in a manner analogous to Example 3. Pale yellow crystals melting at from 79° to 86° C. are obtained.

EXAMPLE 7

Preparation of the adduct of isophorone diisocyanate and the amidine from Example 1

33.3 g (0.15 mol) of isophorone diisocyanate are added portion-wise in the course of 30 minutes to 76.5 g (0.3 mol) of the amidine from Example 1 in a manner analogous to Example 3 at from 120° to 130° C.

Pale yellow crystals melting at from 108° to 113° C. are obtained.

EXAMPLE 8

Preparation of the adduct of hexamethylene diisocyanate and the amidine from Example 2

50.4 g (0.3 mol) of hexamethylene diisocyanate are added portion-wise in the course of 30 minutes to 82.8 g (0.6 mol) of the amidine from Example 2 in a manner analogous to Example 3 at from 130° to 150° C.

Pale yellow crystals melting at from 85° to 90° C. are obtained.

EXAMPLE 9

Preparation of the adduct of isophorone diisocyanate and the amidine from Example 2

44.4 g (0.2 mol) of isophorone diisocyanate are added portion-wise over a period of 30 minutes at from 130° to 185° C. to 55.2 g (0.4 mol) of the amidine from Example 2 in a manner analogous to Example 3.

Pale yellow crystals melting at from 155° to 160° C. are obtained. Isocyanate content 0.2%, by weight.

II. Preparation of the powder lacquers

EXAMPLE 10

38.5 parts of a carboxyl polyester having an acid number of 36 prepared from terephthalic acid (68.64 parts), isophthalic acid (10.27 parts), neopentyl glycol (22.29 parts), ethylene glycol (13.29 parts), and glycerol (2.29 parts) by solvent-free condensation with elimination of water are first mixed dry with 25.6 parts of an epoxide resin of the type of diglycidyl ether of bisphenol A having an epoxide equivalent of 850 and a glass transition temperature of 59° C. (DTA) and with 2.5 parts of the catalyst according to the present invention from Example 4, 33.0 parts of a white pigment of the type of a highly stable titanium dioxide rutile and 0.4 parts of a levelling agent (density 0.975 g/cm$^3$; viscosity 23.3 Pa.s at 20° C.) based on an acrylate oligomer. This mixture is dispersed in the molten state at temperatures of from 80° to 120° C., using a laboratory extruder of Werner & Pfleiderer, Model ZDSK 28. After cooling and preliminary size reduction, the extrudate is ground to a powder lacquer having an average particle size of 50 µm, using a 200 AS blowing mill, spiral jet mill of Alpine, Augsburg. After removal of the coarse particles larger than 100 µm by screening, the powder lacquer which is now ready for use is sprayed on double descaled, degreased test sheets (length 165 mm, width 65 mm, thickness 0.8 mm) using an electrostatic spray device of the type ESB, spray gun Model 50 458 at a negative voltage of ca. 60 kV. The sheets are then stoved in a stoving oven (Kelvi Plast UL 350/S) for 30 minutes at 140° C. The coatings are tested by the conventional methods (see Table I).

The lacquer technical properties were tested in these and the following experiments by the methods outlined below:

(1) Gelling time of powder lacquer according to draft DIN 55 990 Part 8;
(2) Cupping values according to DIN 53 156 (Erichsen);
(3) Impact deformation from the back, based on ASTM G-14, using a weight of 1 kg and a ball of ½ inch diameter; result given in cm.kg (height of fall.weight);
(4) Grid section test according to DIN 53 151;
(5) Degree of gloss according to Gardner, DIN 67 530, 60° angle;
(6) Levelling, visual assessment.

Comparison experiment to Example 10

39.5 parts of the carboxyl polyester from Example 10 are mixed with 26.3 parts of the epoxide resin from Example 10 and 0.8 parts of the unmasked catalyst from Example 2 and with pigment and levelling agent as in Example 10 and made up into a powder lacquer analogously to Example 10. The powder lacquer is applied to test sheets as in Example 10 and then stoved for 30 minutes at 140° C.

For test results see Table I.

EXAMPLE 11

38.9 parts of the carboxyl polyester from Example 10 are mixed with 25.8 parts of the epoxide resin from Example 10, 1.9 parts of the catalyst from Example 3 and pigment and levelling agent as in Example 10 and worked-up into a powder lacquer by the method described in Example 10. The powder lacquer is applied to test sheets as in Example 10 and then stoved for 30 minutes at 140° C. The coatings are tested by the methods described (see Table I).

COMPARISON EXPERIMENT TO EXAMPLE 11

39.5 parts of the carboxyl polyester from Example 10 are mixed with 26.3 parts of the epoxide resin from Example 10, 0.8 parts of the unmasked catalyst from Example 1 and pigment and levelling agent analogously to Example 10 and worked-up into a powder lacquer which is applied to test sheets as in Example 10 and then stoved for 30 minutes at 140° C. (For test results see Table I).

TABLE I

|  |  | Example 10 | Comparison to Example 10 | Example 11 | Comparison to Example 11 |
|---|---|---|---|---|---|
| Gelling time at 180° C. (in sec.) | | 64–65 | 53–54 | 60–61 | 52–53 |
| Cupping values | Stoving | >10 | 9.8 | >10 | >10 |
| Impact deform- | condi- | 20 | 5 | 30 | 10 |

TABLE I-continued

|  |  | Example 10 | Comparison to Example 10 | Example 11 | Comparison to Example 11 |
|---|---|---|---|---|---|
| ation from the back | tions 30 min/ |  |  |  |  |
| Grid section | 140° C. | Gt o/o | Gt o/o | Gt o/o | Gt o/o |
| Degree of gloss |  | 92 | 86 | 92 | 86 |
| Levelling |  | better than in the comparison Example | pronounced texture | better than in the comparison Example | pronounced texture |

EXAMPLE 12

60.81 parts of a commercial carboxyl polyester having an acid number of 31 and a glass transition temperature of 72° C. (DTA) are first mixed dry with 4.58 parts of triglycidyl isocyanurate, 0.81 parts of the catalyst from Example 4, 33.1 parts of a white pigment of the type of a highly stable titanium dioxide rutile and 0.7 parts of the commercial levelling agent from Example 10. This mixture is dispersed as a solvent-free melt at temperatures of from 80° to 120° C., using a double screw extruder, screw diameter 43 mm, 80 revs/min. The extrudate is worked-up into a powder lacquer analogously to Example 10. The powder lacquer obtained is sprayed on test sheets analogously to Example 10 and stoved for 10 minutes at 160° C. (for test results see Table II).

COMPARISON EXPERIMENT TO EXAMPLE 12

61.32 parts of the carboxyl polyester from Example 12 are worked-up into a powder lacquer with 4.62 parts of triglycidyl isocyanurate, 0.26 parts of the catalyst from Example 2 and otherwise the same additives as in Example 12 and sprayed on the test sheets described in Example 10 and subsequently stoved under the same conditions as in Example 12 (for test results see Table II).

EXAMPLE 13

60.98 parts of the carboxyl polyester from Example 12, 4.59 parts of triglycidyl isocyanurate, 0.63 parts of the catalyst from Example 3, 33.1 parts of a commercial, highly stable rutile titanium dioxide type pigment and 0.7 parts of a commercial levelling agent are worked-up into a powder lacquer as in Example 10. The lacquer obtained is sprayed on test sheets analogously to Example 10 and stoved for 10 minutes at 160° C. (for test results see Table II).

COMPARISON EXPERIMENT TO EXAMPLE 13

61.32 parts of the carboxyl polyester from Example 12 are worked-up with 4.62 parts of triglycidyl isocyanurate, 0.26 parts of the catalyst from Example 1 and otherwise the same additives as in Example 13 to produce a powder lacquer which is sprayed on test sheets and subsequently stoved under the same conditions as in Example 13 (for test results see Table II).

TABLE II

|  |  | Example 12 | Comparison to Example 12 | Example 13 | Comparison to Example 13 |
|---|---|---|---|---|---|
| Gelling time at 180° C. (sec) |  | 53-54 | 66-67 | 58-59 | 57-59 |
| Cupping values | Stoving conditions | 10 | 10 | 10 | 10 |
| Impact deformation from the back | 10 min/160° C. | 50 | 40 | 60 | 90 |
| Grid section |  | Gt o/o | Gt o/o | Gt o/o | Gt o/o |
| Degree of Gloss |  | 84 | 74 | 84 | 67 |
| Levelling |  | better than in the comparison Example | pronounced texture | better than in the comparison Example | pronounced texture |

EXAMPLE 14

60.9 parts of a commercial carboxyl polyester having an acid number of 31 and a glass transition temperature of 66° C. (DTA) are worked-up with 4.6 parts of triglycidyl isocyanurate, 0.7 parts of the catalyst from Example 5, 33.1 parts of a commercial, highly stable rutile titanium dioxide type pigment and 0.7 parts of a commercial levelling agent to produce a powder lacquer analogously to Example 10. The powder lacquer obtained is sprayed on test sheets as in Example 10 and stoved for 10 minutes at 160° C. (for test results see Table III).

COMPARISON EXPERIMENT TO EXAMPLE 14

61.31 parts of the carboxyl polyester from Example 14, 4.63 parts of triglycidyl isocyanate, 0.26 parts of the commercial product, tetramethyl guanidine, and otherwise the same additives as used in Example 14 are worked-up into a powder lacquer which is sprayed on test sheets and then stoved under the same conditions as in Example 14 (for test results see Table III).

TABLE III

|  |  | Example 14 | Comparison to Example 14 |
|---|---|---|---|
| Gelling time at 180° C. (sec) |  | 52-53 | 47-49 |
| Depth of cupping | Stoving conditions | 10 | >10 |
| Impact deformation from the back | 10 min/ 160° C. | 70 | 50 |
| Grid section |  | Gt o/o | Gt o/o |

TABLE IV

|  | Example 15 | Comparison to Example 15 | Example 16 | Comparison to Example 16 |
|---|---|---|---|---|
| Gelling time at 180° C. (sec) | 51–53 | 53–54 | 59–62 | 52–53 |
| Cupping values — Stoving conditions 30 min/140° C. | 10 | 9.8 | 10 | >10 |
| Impact deformation from the back | 5 | 5 | 30 | 10 |
| Grid section | Gt o/o | Gt o/o | Gt o/o | Gt o/o |
| Degree of gloss | 89 | 86 | 94 | 88 |
| Levelling | better than in the comparison experiment | pronounced texture | better than in the comparison experiment | pronounced texture |

TABLE III-continued

|  | Example 14 | Comparison to Example 14 |
|---|---|---|
| Degree of gloss | 85 | 80 |
| Levelling | slight orange peel texture | short grained texture |

EXAMPLE 15

39.2 parts of the carboxyl polyester from Example 10 are mixed with 26.1 parts of the epoxide resin from Example 10, 1.3 parts of the catalyst from Example 8 and pigment and levelling agent as in Example 10 and worked-up into a powder lacquer by the method described in Example 10. The powder lacquer is applied to test sheets as in Example 10 and then stoved for 30 minutes at 140° C. (for test results see Table IV).

COMPARISON EXPERIMENT TO EXAMPLE 15

39.5 parts of the carboxyl polyester from Example 10 are mixed with 26.3 parts of the epoxide resin from Example 10, 0.8 parts of unmasked catalyst from Example 2 and pigment and levelling agent as in Example 10 and worked-up into a powder lacquer by the method described in Example 10. The powder lacquer is applied to test sheets as in Example 10 and stoved for 30 minutes at 140° C. (for test results see Table IV).

EXAMPLE 16

39.4 parts of the carboxyl polyester from Example 10 are mixed with 26.1 parts of the epoxide resin from Example 10, 1.1 parts of the catalyst from Example 6 and pigment and levelling agent as in Example 10 and worked-up into a powder lacquer by the method described in Example 10. The powder lacquer is applied to test sheets as in Example 10 and then stoved for 30 minutes at 140° C. (for test results see Table IV).

COMPARISON EXPERIMENT TO EXAMPLE 16

39.5 parts of the carboxyl polyester from Example 10 are mixed with 26.3 parts of the epoxide resin from Example 10, 0.8 parts of the unmasked catalyst from Example 1 and pigment and levelling agent as in Example 10 and worked-up into a powder lacquer by the method described in Example 10. The powder lacquer is applied to test sheets as in Example 10 and then stoved for 30 minutes at 140° C. (for test results see Table IV).

EXAMPLE 17

60.9 parts of the carboxyl polyester from Example 12, 4.6 parts of triglycidyl isocyanurate, 0.7 parts of the catalyst from Example 9, 33.1 parts of a white pigment of the type of a highly stable titanium dioxide rutile, and 0.7 parts of a commercial levelling agent are worked-up into a powder lacquer analogously to Example 10. The powder lacquer obtained is sprayed on test sheets as in Example 10 and stoved for 10 minutes at 160° C. (for test results see Table V).

COMPARISON EXPERIMENT TO EXAMPLE 17

61.32 parts of the carboxyl polyester from Example 17, 4.62 parts of triglycidyl isocyanurate, 0.26 parts of the catalyst from Example 2 and otherwise the same additives as in Example 17 are worked-up into a powder lacquer analogously to Example 17. The powder lacquer is sprayed on the test sheets described in Example 10 and then stoved under the same conditions as in Example 17 (for test results see Table V).

EXAMPLE 18

60.90 parts of the carboxyl polyester from Example 14 are mixed with 4.6 parts of triglycidyl isocyanurate, 0.7 parts of the catalyst from Example 7, 33.1 parts of a commercial, highly stable rutile titanium dioxide type of pigment and 0.7 parts of a commercial levelling agent, and extruded and worked-up into a powder lacquer analogously to Example 10. The powder lacquer obtained is sprayed on test sheets as in Example 10 and stoved for 10 minutes at 160° C. (for test results see Table V).

COMPARISON EXPERIMENT TO EXAMPLE 18

61.12 parts of the carboxyl polyester from Example 18 are worked-up into a powder lacquer with 4.62 parts of the polyepoxide from Example 18, 0.46 parts of the catalyst from Example 1 and otherwise the same additives as in Example 18. The powder lacquer is sprayed on the test sheets described in Example 10 and then stoved under the same conditions as in Example 18 (for test results see Table V).

TABLE V

|  | Example 17 | Comparison to Example 17 | Example 18 | Comparison to Example 18 |
|---|---|---|---|---|
| Gelling time at 180° C. (sec) | 54–55 | 63–65 | 76–79 | 43–45 |
| Cupping values — Stoving conditions 10 min/160° C. | 10 | 10 | 10 | 10 |
| Impact deformation from the back | 130 | 10 | 80 | 70 |

| | Example 17 | Comparison to Example 17 | Example 18 | Comparison to Example 18 |
|---|---|---|---|---|
| Grid section | Gt o/o | Gt o/o | Gt o/o | Gt o/o |
| Degree of gloss | 83 | 78 | 85 | 77 |
| Levelling | better than in comparison experiment | pronounced texture | better than in comparison experiment | pronounced texture |

We claim:

1. Addition products obtainable from monoisocyanates having from 2 to 20 carbon atoms and tetrahydropyrimidines of the formula

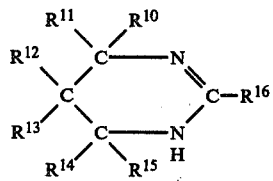

wherein $R^{10}$ to $R^{16}$ are each hydrogen, alkyl having from 1 to 6 carbon atoms, cycloalkyl having from 5 to 10 carbon atoms, aralkyl having from 7 to 12 carbon atoms, aryl having from 6 to 15 carbon atoms, and also together two geminal or vicinal substituents $R^{10}$ to $R^{16}$ together with the carbon atom to which they are attached comprise a cycloaliphatic ring having 5 to 6 carbon atoms.

2. Addition products according to claim 1 wherein the tetrahydropyrimidines are selected from 2-methyl-tetrahydropyrimidine, 2,4-, 2,5- and 2,6-dimethyl-tetrahydropyrimidine, 2-ethyl-tetrahydropyrimidine, 2-ethyl-4-methyl-tetrahydropyrimidine, 2-benzyl-tetrahydropyrimidine, 2-phenyl-tetrahydropyrimidine, 2-phenyl-4-methyl, -5-methyl- and -6-methyl-tetrahydropyrimidine, 2,4-diaza-3-phenyl-7,9,9- and 7,7,9-trimethyl-bicyclo-(4,3,0)-nonene-2, and 2,4-diaza-3-methyl-7,9,9- and 7,7,9-trimethyl-bicyclo(4,3,0)-nonene-2 and mixtures thereof.

* * * * *